(12) United States Patent
Stangl et al.

(10) Patent No.: US 12,140,257 B2
(45) Date of Patent: *Nov. 12, 2024

(54) ASEPTIC FLUID COUPLINGS

(71) Applicant: Colder Products Company, Roseville, MN (US)

(72) Inventors: Jack T. Stangl, Falcon Heights, MN (US); Loi T. Truong, Savage, MN (US)

(73) Assignee: Colder Products Company, Roseville, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/125,338

(22) Filed: Mar. 23, 2023

(65) Prior Publication Data

US 2023/0400135 A1    Dec. 14, 2023

Related U.S. Application Data

(60) Provisional application No. 63/344,786, filed on May 23, 2022.

(51) Int. Cl.
*F16L 37/36* (2006.01)
*A61M 39/26* (2006.01)
*F16L 37/098* (2006.01)

(52) U.S. Cl.
CPC ............ *F16L 37/36* (2013.01); *A61M 39/26* (2013.01); *A61M 2205/273* (2013.01); *F16L 37/0982* (2013.01); *F16L 2201/44* (2013.01)

(58) Field of Classification Search
CPC ....... F16L 37/36; F16L 37/32; F16L 37/0982; F16L 2201/44; A61M 39/26; A61M 2205/273

See application file for complete search history.

(56) References Cited

U.S. PATENT DOCUMENTS 2,203,922 A * 6/1940 Paisley .................. F16L 37/36
                                                      251/148
4,334,551 A * 6/1982 Pfister .................. A61M 39/26
                                                      604/905

(Continued)

FOREIGN PATENT DOCUMENTS

WO    WO 2020/240150         4/2020
WO    WO 2020/251883         12/2020
WO    WO-2020251883 A1 * 12/2020  .......... F16L 37/0841

OTHER PUBLICATIONS

International Search Report and Written Opinion in International Appln. No. PCT/US2023/016050, mailed on Jun. 28, 2023, 14 pages.

(Continued)

*Primary Examiner* — David Colon-Morales
(74) *Attorney, Agent, or Firm* — Fish & Richardson P.C.

(57) ABSTRACT

Some fluid coupling devices described herein are configured for use in fluid systems for purposes of providing a single-use, aseptic disconnection functionality that substantially prevents fluid spillage when being disconnected. In some embodiments, the coupling portions cannot be functionally reconnected to each other after being disconnected from each other. Some fluid coupling device embodiments described herein include a fluid flow path that is a metallic-free. Moreover, some embodiments of the fluid coupling devices provided herein include no metal whatsoever. That is, the fluid coupling devices are entirely metallic-free.

17 Claims, 15 Drawing Sheets

(56) References Cited

U.S. PATENT DOCUMENTS

| | | | | |
|---|---|---|---|---|
| 4,499,932 A * | 2/1985 | Perigo | F16L 37/36 | 141/348 |
| 5,820,614 A * | 10/1998 | Erskine | F16L 55/1007 | 604/905 |
| 7,396,051 B2 * | 7/2008 | Baldwin | A61M 39/26 | 604/905 |
| 7,631,660 B2 * | 12/2009 | deCler | F16L 37/098 | 137/614.05 |
| 8,152,203 B2 * | 4/2012 | Olivier | F16L 37/36 | 604/905 |
| 8,690,120 B2 * | 4/2014 | Hartnett | F04B 39/0005 | 604/533 |
| 8,746,278 B2 * | 6/2014 | Py | F16L 37/36 | 251/340 |
| 8,899,267 B2 * | 12/2014 | Diodati | A61M 39/18 | 137/614.04 |
| 9,901,729 B2 * | 2/2018 | Vigna | A61M 39/18 | |
| 9,909,703 B2 * | 3/2018 | Van Scyoc | F16L 37/32 | |
| 10,022,532 B2 * | 7/2018 | Burdge | A61M 39/18 | |
| 10,864,364 B2 * | 12/2020 | Mack | A61M 39/26 | |
| 11,480,281 B2 * | 10/2022 | Benson | A61M 39/1011 | |
| 11,566,736 B2 * | 1/2023 | Truong | A61M 39/1011 | |
| 2014/0345748 A1 * | 11/2014 | Rogers | A61J 1/12 | 141/330 |
| 2017/0202741 A1 * | 7/2017 | Py | A61M 39/18 | |
| 2018/0296817 A1 | 10/2018 | Burdge | | |
| 2020/0297990 A1 | 9/2020 | Vigna et al. | | |
| 2020/0347977 A1 | 11/2020 | Dornburg | | |
| 2021/0199220 A1 | 7/2021 | Truong | | |
| 2021/0388926 A1 | 12/2021 | Martin et al. | | |
| 2021/0388930 A1 | 12/2021 | Benson | | |
| 2023/0213129 A1 * | 7/2023 | Peabody | A61M 39/18 | |
| 2023/0375116 A1 * | 11/2023 | Stangl | F16L 37/36 | |

OTHER PUBLICATIONS

International Search Report and Written Opinion in International Appln. No. PCT/US2023/023065, mailed on Aug. 23, 2023, 14 pages.

* cited by examiner

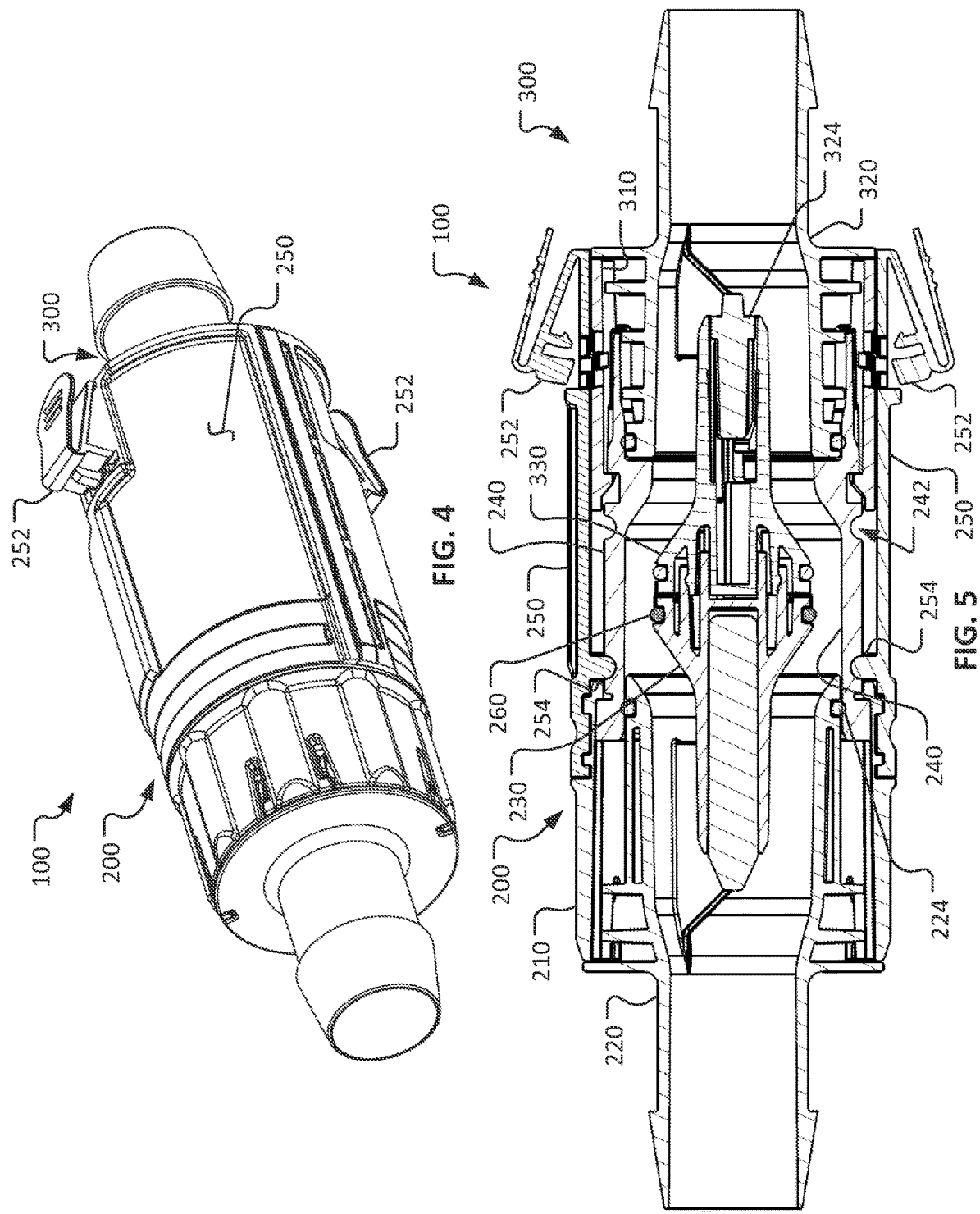

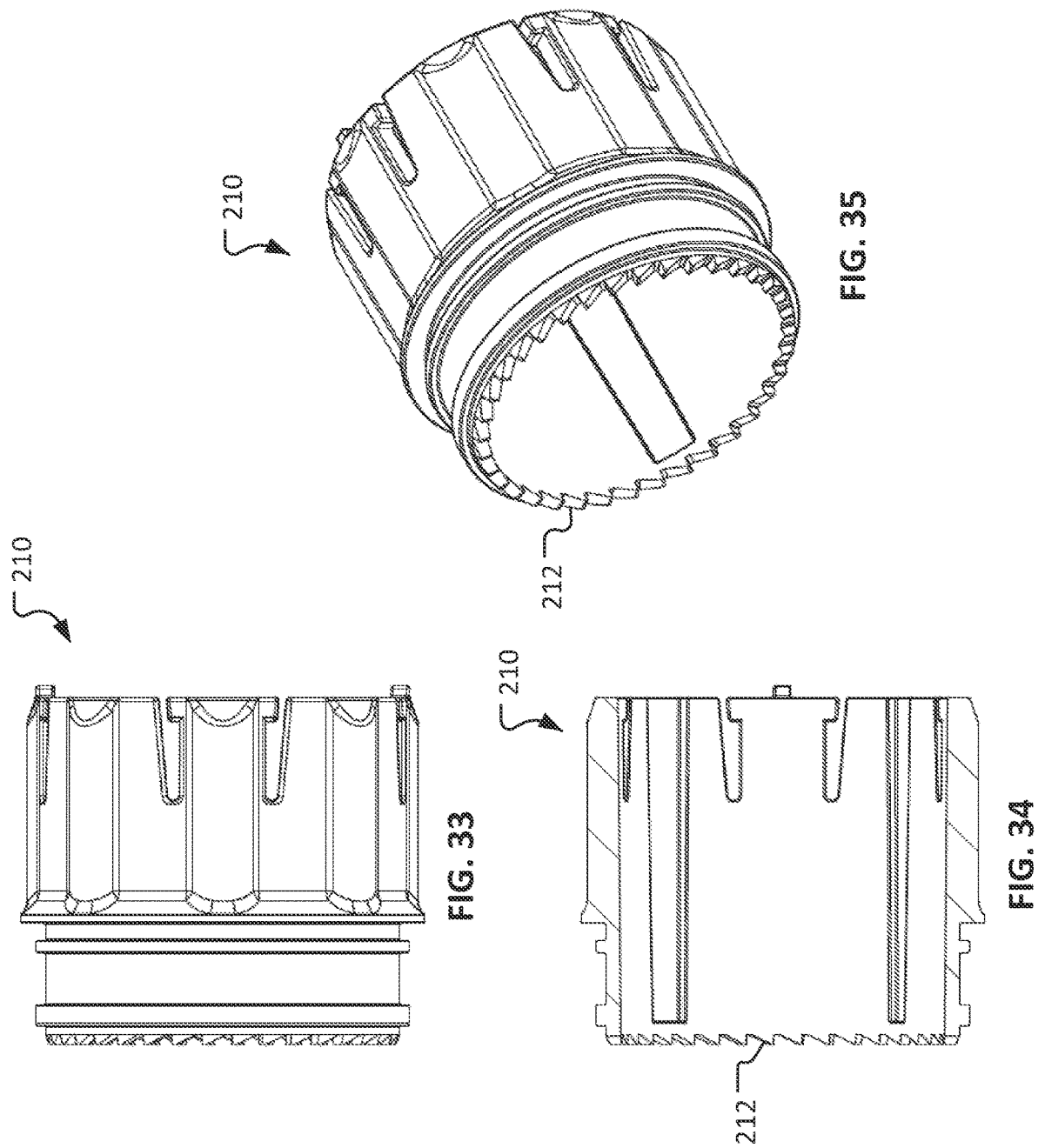

ASEPTIC FLUID COUPLINGS

CROSS-REFERENCE TO RELATED APPLICATIONS

This application claims the benefit of U.S. Provisional Application Ser. No. 63/344,786, filed May 23, 2022. The disclosure of the prior application is considered part of (and is incorporated by reference in) the disclosure of this application.

BACKGROUND

1. Technical Field

This document relates to fluid coupling devices for fluid systems and methods. For example, some embodiments described in this document relate to single-use, aseptic disconnection fluid coupling devices.

2. Background Information

Fluid systems commonly include components such as tubing, pumps, reservoirs, fittings, couplings, heat exchangers, sensors, filters, valves, seals, and the like. Such components can be connected together in a network to define one or more fluid flow paths.

Fluids may be moved through fluid systems using fluid pressure differentials. For example, in some cases, a pump or a vacuum source is used to create a pressure differential that causes the fluid to flow within the fluid system. In another example, gravity is used to cause the fluid to flow within the fluid system. In still other examples, mechanical means can be used to exert exterior force on a tube or reservoir causing fluid to flow. A peristaltic pump is one example. In other examples, a combination of such techniques is used to cause the fluid to flow within the fluid system.

Some fluid couplings can be used for sterile fluid conveyance, such as for connecting a source of one or more sterile ingredients to a sterile processing system, such as a bioreactor or other type of sterile system or container. Fluid couplings for sterile fluid conveyance can also be used for extracting samples from a sterile processing system. Fluid couplings for sterile fluid conveyance can also be used to connect together two or more pieces of sterile processing equipment.

In the context of some fluid systems, such as some bioprocessing fluid systems, it may be desirable to have a tube coupling that can aseptically disconnect a fluid flow path. In one such example implementation, it is desirable to disconnect aseptically one or more containers (e.g., media bags) from a bioreactor system. In that scenario, an aseptic coupling can be used to disconnect the container(s) from the bioreactor system while substantially preventing biological contamination of the containers, of tubing, of other connected components, and of the bioreactor via the disconnected ends of the coupling during and after the disconnection process. Such an aseptic coupling will also serve to limit the exposure of the fluid to the surrounding environment.

SUMMARY

This document describes fluid coupling devices for fluid systems and methods. In some embodiments, the fluid coupling devices can be implemented as single-use, aseptic disconnection fluid coupling devices that are configured to reduce the likelihood of fluid spillage when being disconnected. In some embodiments, the coupling portions cannot be reconnected to each other (or to other couplings) after being disconnected from each other. Accordingly, the fluid coupling devices are called "single-use" aseptic disconnect couplings.

In the context of this disclosure, the term "fluid" means any substance that can be made to flow including, but is not limited to, liquids, gases, granular or powdered solids, mixtures or emulsions of two or more fluids, suspensions of solids within liquids or gases, vapors, steam, mists, gels, semi-solids, etc.

In particular embodiments, the fluid coupling devices described herein are single-use devices because, after the two portions of the coupling (also referred to herein as "coupling halves," "connectors," or a "body" and an "insert") are disconnected from each other, the fluid paths of one or both portions are irreversibly blocked. Hence, in these particular embodiments, the fluid coupling devices provided herein are structurally configured to be single-use disconnection devices so that, after the single-use coupling halves have been disconnected from each other, they cannot be operably reconnected to each other (or to any other coupling halves) so as to reestablish an open fluid flow path therethrough, and/or cannot be mechanically reconnected to each other.

Additionally, in such single-use embodiments or in other embodiments, the fluid coupling devices can be configured as "aseptic" coupling devices in that, during disconnection and after the two portions of the coupling device are disconnected from each other, the fluid paths of both portions are mechanically blocked, e.g., by a valve, so as to inhibit biological contamination migrating into the flow paths. In some such embodiments, the mechanical blocking of the fluid paths is irreversible, e.g., the valves cannot be opened by reversing the actions that were taking during the disconnection process. Such an "aseptic" coupling will also serve to limit the exposure of the fluid to the surrounding environment. As used herein, the term "aseptic" refers to any process or device that maintains a sterilized surface or volume. "Sterile" as used herein refers to being free from bacteria or other living microorganisms, or being/having below a particular level of bacteria or other living microorganisms.

Further, in such single-use embodiments, or other embodiments, the fluid coupling devices can be configured as no-spill coupling devices because, as the two portions of the coupling device are being disconnected from each other, one or more mechanical components will reduce the likelihood of fluid discharge out of the fluid system (for example, by blocking such discharge paths), and/or by preventing spillage by limiting fluid inclusion incurred when the couplings are used and/or when the couplings are connected to each other.

Particular embodiments of the subject matter described in this document can be implemented to realize one or more of the following advantages. First, the coupling halves of the fluid coupling devices provided herein are designed so that the uncoupling process involves closing valves in a particular sequence so that spillage (discharge) of fluid is eliminated or minimized (i.e., a non-spill disconnection capability). Accordingly, contamination of the surrounding environment can be prevented.

Second, in some embodiments, the fluid coupling devices are designed to be used with tubing that is relatively large (e.g., diameters of ¼ inch and larger, sanitary fittings that are ¾ inch and larger, and so on), and to provide flow characteristics consistent with such large diameter tubing.

Third, some embodiments of the fluid coupling devices provide an improved aseptic disconnection capability that may optionally reduce or eliminate the need for sterile rooms or sterile benchtop environments in some cases. As such, these embodiments of the aseptic fluid coupling devices described herein may facilitate efficient and cost-effective operations or uses that would otherwise be high-cost or even cost prohibitive in some traditional settings that required the disconnection of particular fluid couplings in a sterile room or within a sterile flow-hood to prevent biological contamination.

Fourth, some embodiments of the fluid coupling devices provided herein are advantageously designed to be single use couplings that cannot be operatively reconnected to reestablish an open flow path therethrough. Accordingly, the potential for contamination from reuse is prevented.

Fifth, some embodiments of the fluid coupling devices provided herein include a fluid flow path that is a metallic-free. Moreover, some embodiments of the fluid coupling devices provided herein include no metal whatsoever. That is, the fluid coupling devices are entirely metallic-free.

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 4 is a perspective view of the fluid coupling system of FIG. 1 configured in a first stage of disconnection.

FIG. 5 is a longitudinal cross-section view of the fluid coupling system configured as in FIG. 4.

FIGS. 33-35 show various views of a body housing component of the fluid coupling system of FIG. 1.

Like reference numbers represent corresponding parts throughout.

DETAILED DESCRIPTION OF ILLUSTRATIVE EMBODIMENTS

Figure 1:
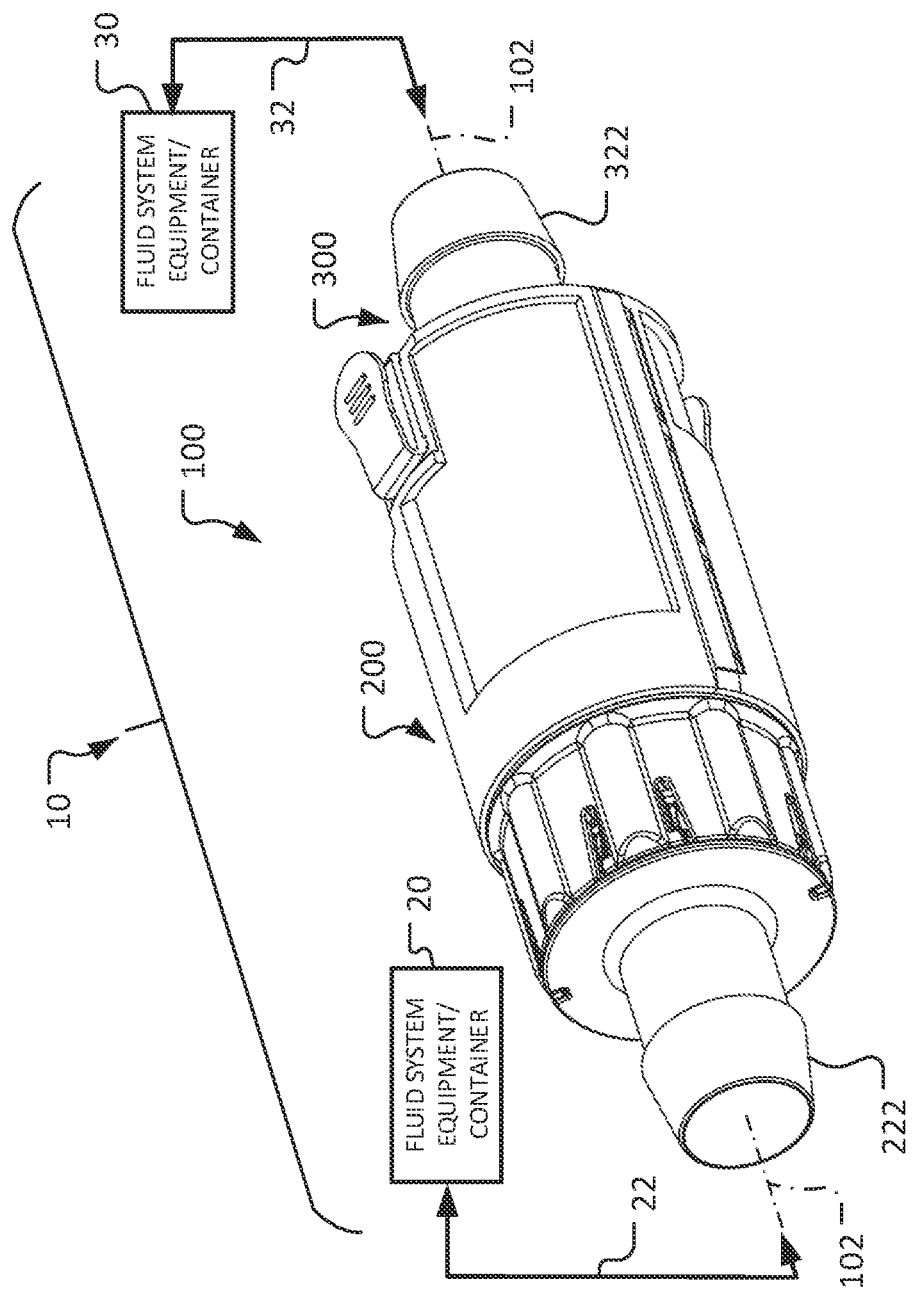
FIG. 1 is a schematic depiction of a fluid system that uses an example fluid coupling system in accordance with some embodiments described herein.
Figure 2:
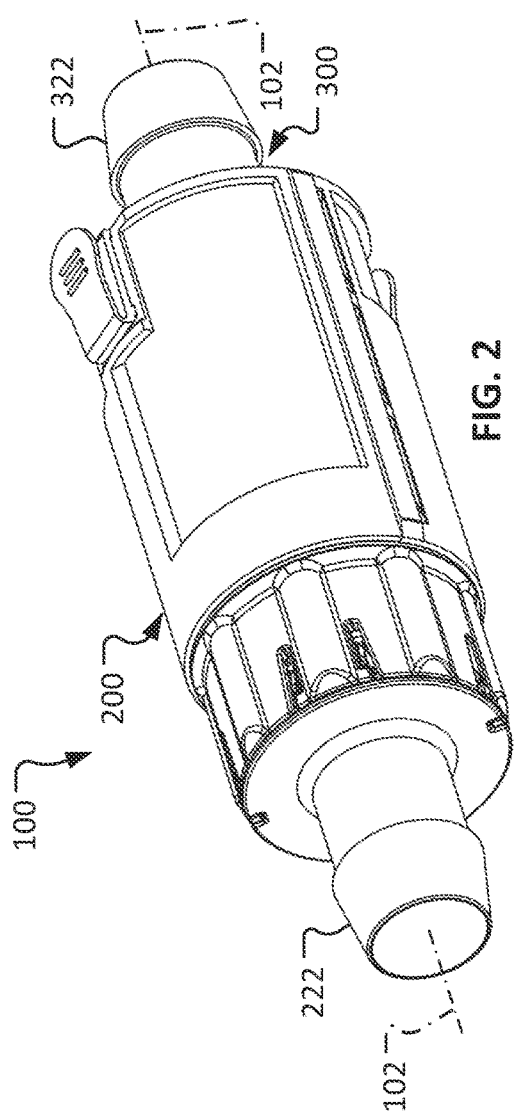
FIG. 2 is a perspective view of the fluid coupling system of FIG. 1.
Figure 3:
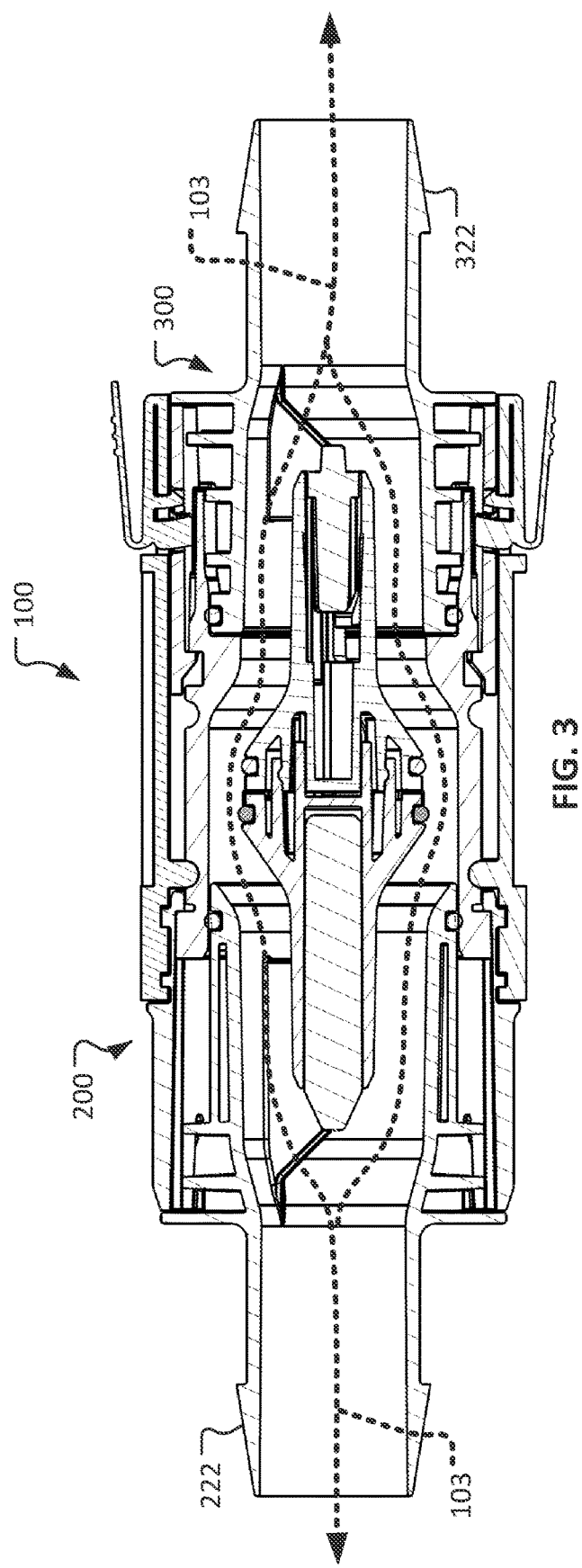
FIG. 3 is a longitudinal cross-section view of the fluid coupling system of FIG. 1 in an operable configuration.

Referring to FIGS. 1-3, some example embodiments of a fluid system 10 include an example fluid coupling assembly 100 configured to, for example, releasably connect a first fluid system equipment or container 20 to a second fluid system equipment or container 30. In some implementations, the fluid system 10 may include at least one fluid coupling assembly 100 that is a single-use, aseptic disconnection fluid coupling device. The fluid coupling assembly 100 (or more simply, the "fluid coupling 100") defines a longitudinal axis 102 (FIGS. 1 and 2), and an open fluid flow path 103 (FIG. 3) through the fluid coupling device 100 along the longitudinal axis 102. The depicted configuration of the fluid coupling assembly 100 in which the open fluid flow path 103 exists is also referred to herein as the "open configuration" or the "operable configuration."

In one non-limiting example, the fluid coupling 100 can provide a single-use, aseptic disconnection capability for a fluid path between the fluid system equipment in the form of a bioreactor system (connected directly to the coupling device 100 or connected via a fluid tube 22) and the fluid system container 30 in the form of a media bag (connected directly to the coupling device 100 or connected via a fluid tube 32).

In the depicted embodiment, the fluid coupling assembly 100 includes a first coupling 200 and a second coupling 300. After the fluid transfer functionality of the fluid coupling assembly 100 has been used, the fluid coupling assembly 100 can be disconnected. That is, a user can disconnect the fluid coupling assembly 100 by separating the first coupling 200 and the second coupling 300 in accordance with a prescribed technique (e.g., see FIGS. 4-11). This systematic disconnection process is described in further detail below.

The first coupling 200 and the second coupling 300 are configured to disconnect from one another in a manner that provides an aseptic disconnection, and that mechanically prevents reconnection and reuse of the fluid flow path 103 through the first coupling 200 and the second coupling 300. As used herein, the term "aseptic" refers to any process that maintains a sterilized surface or volume. The first coupling 200 and the second coupling 300 are sometimes referred to herein as "coupling halves" or a "coupling-half" even though the first coupling 200 and the second coupling 300 are not necessarily equal halves in terms of size, shape, weight, features, or functionality.

In some cases, the fluid coupling assembly 100 is provided to the end user in a sterile condition, or is made to be compatible with sterilization. As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies. As used herein, the term "aseptic" refers to any process that maintains a sterilized surface or volume. In some cases, the fluid coupling device 100 is provided to the end user as a component of a system.

Generally, the fluid coupling assembly 100 is provided to an end user in the coupled arrangement, with the coupled mating coupling halves 200 and 300, as depicted in FIGS. 1-3. The end user will use the fluid coupling assembly 100 in the coupled arrangement, and then after such use will disconnect the first coupling 200 and the second coupling 300 from each other. When the disconnection is performed, the fluid flow paths 103 in each of the coupling halves 200 and 300 are aseptically sealed in a closed state. In addition, as the disconnection of the coupling halves 200 and 300 is performed, no fluid (or only a minimal amount of fluid) is spilled to the area external to the fluid coupling assembly 100 during the disconnection process.

The first coupling 200 includes a first termination 222. The second coupling 300 includes a second termination 322. While the first and second terminations 222 and 322 are depicted as barbed connections, it should be understood that the coupling halves 200 and 300 can have any type of connections such as, but not limited to, threaded connections (e.g., straight thread or pipe thread), sanitary fittings, compression fittings, aseptic connections, quick connects, quick disconnects, hydraulic connections, luer fittings, solder connections, welded connections, and the like, and combinations thereof. Such connections can be straight (as depicted) or in another arrangement such as, but not limited to, a 90° elbow arrangement, a 45° elbow, a straight fitting, a Tee fitting, a Y-fitting, and so on. In some embodiments, the coupling halves 200 and/or 300 can be configured to be fluidly coupled with a fluid conduit such as, but not limited to, a tube, pipe, a manifold, and the like, without limitation.

The materials from which one or more of the components of the fluid coupling assembly 100 are made of include thermoplastics or thermosets. In particular embodiments, the materials from which the components of the fluid coupling assembly 100 are made of are thermoplastics, such as, but not limited to, acetal, ABS, polycarbonate, polysulfone, polyether ether ketone, polysulphide, polyester, polyvinylidene fluoride (PVDF), polyethylene, Perfluoropolymers (PFA, PTFE, PCTFE and the like), polyphenylsulfone (PPSU; e.g., Radel®), polyetherimide (PEI; e.g., Ultem®), polypropylene, polyphenylene, polyaryletherketone, Perfluoropolymers (PFA, PTFE, PCTFE and the like) and the like, and combinations thereof. In some embodiments, the thermoplastics can include one or more fillers such as, but not limited to, glass fiber, glass bead, carbon fiber, talc, etc.

In some embodiments, the materials from which one or more of the components of the fluid coupling assembly 100 are made of include metals such as, but not limited to, stainless steel, brass, aluminum, plated steel, zinc, and the like. In particular embodiments, one or both of the coupling halves 200 and 300 is/are metallic-free.

In some embodiments, one or both of the coupling halves 200 and/or 300 includes one or more plastic (e.g., PEEK, PPS, etc.) or metallic spring members (e.g., spring steel, stainless steel such as 316L, piano/music wire, beryllium copper, titanium, Hastelloy®, Inconel®, and the like).

In certain embodiments, fluid coupling assembly 100 includes one or more gaskets or seals that are made of materials such as, but not limited to, silicone, fluoroelastomers (FKM), ethylene propylene diene monomer (EPDM), perfluoroelastomers (e.g., FFKM, Kalrez®, Chemraz® and the like), thermoplastic elastomers (TPE), bung, buna-N, thermoplastic vulcanizates (TPV), and the like. In some embodiments, the gaskets or seals can have a cross-sectional shape that is an hourglass-shape, an oval shape, a circular shape, D-shaped, X-shaped, square, rectangular, U-shaped, L-shaped, V-shaped, a polygonal shape, a multi-lobe shape, or any other suitable shape, without limitation.

FIGS. 4-11 illustrate the process of disconnecting the coupling halves 200 and 300. The components of the fluid coupling assembly 100 are designed so that the steps described below for disconnecting the coupling halves 200 and 300 can only be performed in the sequence described. That is, the fluid coupling assembly 100 includes mechanical structures that prevent any of the steps from being performed out of sequence. Moreover, when a step is completely performed, the step cannot be reversed. The fluid coupling assembly 100 includes mechanical structures that latch the components in the various positions associated with the completion of each of the sequential steps of the disconnection process.

The sequence of steps to disconnect the coupling halves 200 and 300 will ensure that the fluid flow paths of the coupling halves 200 and 300 (e.g., the fluid flow path 103 shown in FIG. 3) are fluidly sealed closed prior to the separation of the coupling halves 200 and 300. Accordingly, the fluid flow paths of the coupling halves 200 and 300 are prevented from becoming contaminated. In addition, no fluid (or only minimal fluid) is spilled or released when the coupling halves 200 and 300 are separated.

Referring to FIGS. 4 and 5 in particular, the coupling half 200 includes a shell 250 that surrounds a portion of the coupling half 200. The shell 250 is manually rotatable in relation to the fluid coupling assembly 100. As described further below, manual rotation of the shell 250 about the longitudinal axis 102 of the fluid coupling assembly 100 is what drives the closure of valves in each of the coupling halves 200 and 300 and the physical separation of the coupling halves 200 and 300.

Figure 13:
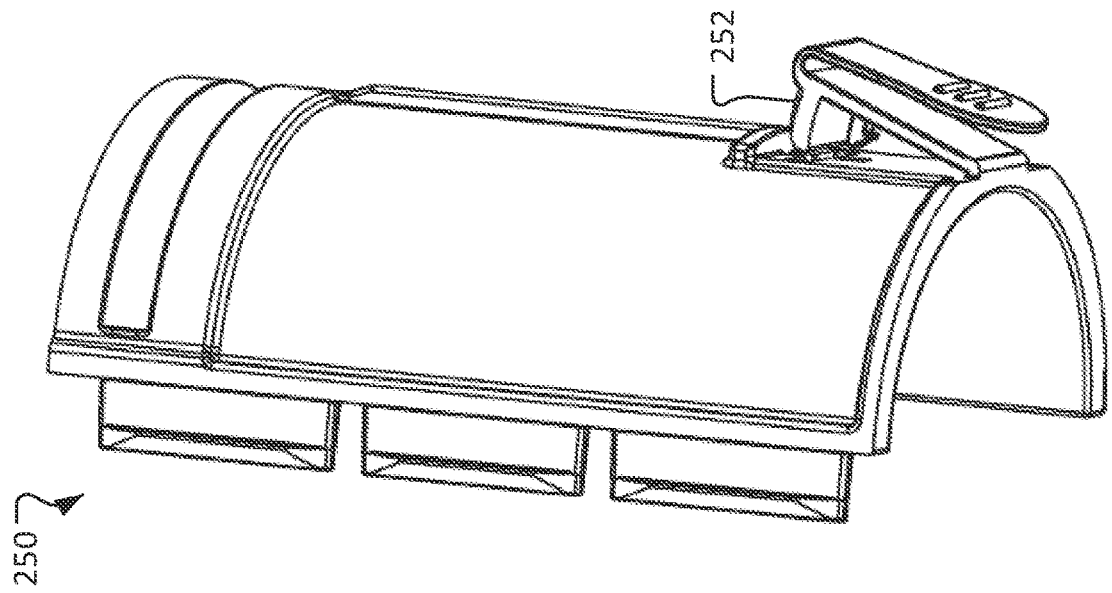
FIGS. 12 and 13 show various views of a shell component of the fluid coupling system of FIG. 1.
Figure 12:
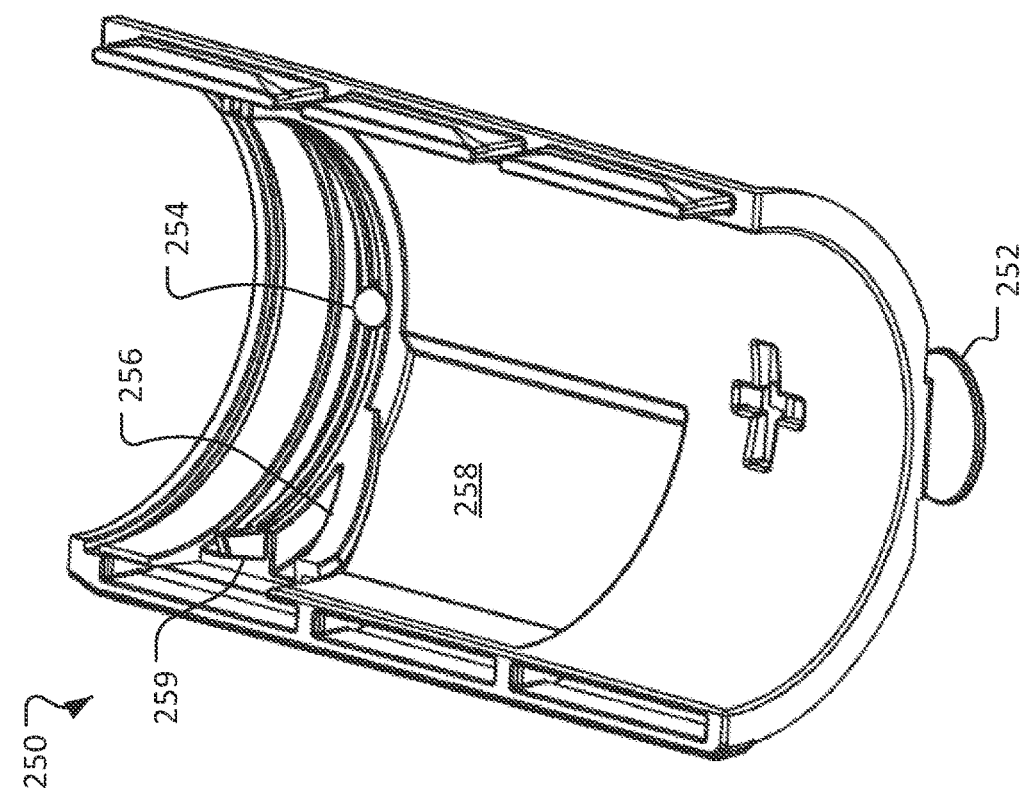

Referring also to FIGS. 12 and 13, here a half of the shell 250 is shown in isolation so that the features of the shell 250 can be more clearly visualized. The shell 250 includes two of the half shells that are illustrated. That is, in the depicted embodiment of the coupling half 200 two identical half shells are joined together to create a cylindrical shell 250 that is rotatably coupled to the coupling half 200. In some embodiments, the components that make up the shell 250 may be dissimilar from each other. In the depicted embodiment, the two identical half shells are mechanically snapped together to create the cylindrical shell 250. In some embodiments, other joining techniques can be used, or the shell 250 can be created as a single unitary component.

As shown in FIGS. 4, 5, 12, and 13, the shell includes two latching tabs 252. The latching tabs 252 releasably engage with the coupling half 300. When the latching tabs 252 are engaged with the coupling half 300, the shell 250 cannot be rotated in relation to the fluid coupling assembly 100. FIGS. 1-3 show the latching tabs 252 in engagement with the coupling half 300.

The first step of the sequence of steps to disconnect the coupling halves 200 and 300 is disengagement of the latching tabs 252 from the coupling half 300. This is illustrated in FIGS. 4 and 5. In the depicted embodiment, the latching tabs 252 are manually pivoted radially outward to disengage the latching tabs 252 from the coupling half 300. Other types of disengagement mechanisms and techniques (other than pivoting the latching tabs 252) can be used in some embodiments. For example, in some embodiments the disengagement mechanism can be (or can comprise) a removable locking tab(s), a spring-loaded clip, a pinch and release mechanism, a push and release mechanism, a tear-away ring component that locks the shell 250 with the insert housing 310 and shuttle 240 during operation, a deflectable feature (such as a cantilever—the user would deflect the feature to remove interference and allow rotation). Another disengagement mechanism would be a feature that could be translated—such as a slide latch on each side that moves axially, or a single ring that interfaces both slots and is pulled back/moved axially to allow rotation.

The shell 250 can be considered an anti-tamper sleeve or anti-taper guard because while the latching tabs 252 are engaged with the coupling half 300 no other step for disconnecting the coupling halves 200 and 300 can be performed. Accordingly, the unlatching of the latching tabs 252 from the coupling half 300 must be the first step in the sequence of steps required to disconnect the coupling halves 200 and 300.

The first step in the sequence of steps to disconnect the coupling halves 200 and 300 is completed with the disengagement of the latching tabs 252.

Figure 6:
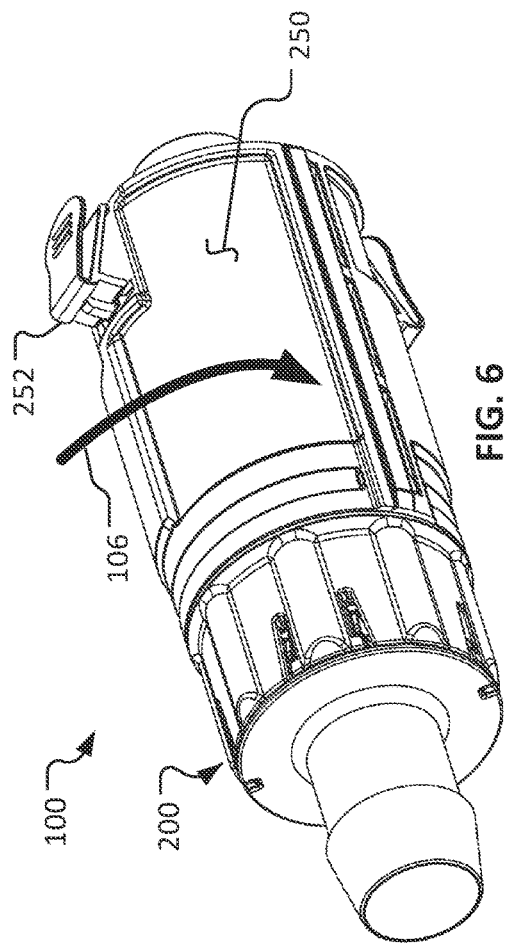
FIG. 6 is a perspective view of the fluid coupling system of FIG. 1 configured in a second stage of disconnection.
Figure 7:
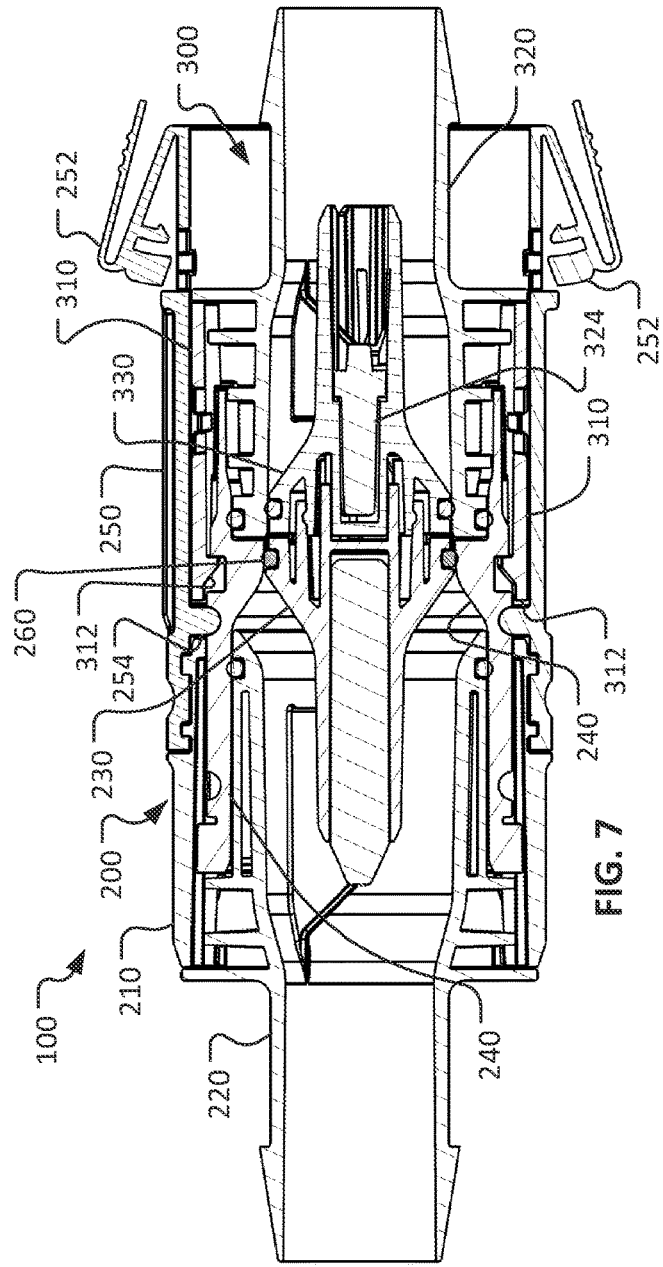
FIG. 7 is a longitudinal cross-section view of the fluid coupling system configured as in FIG. 6.

Referring to FIGS. 6 and 7, with the latching tabs 252 disengaged from the coupling half 300, the next step of the sequence of steps to disconnect the coupling halves 200 and 300 is the manual rotation of the shell 250 as indicated by the arrow 106 in FIG. 6 (which, in other embodiments, can be made to be rotated in the opposite direction). The rotation of the shell 250 closes valves in each of the coupling halves 200 and 300 so that the previously open fluid flow path 103 becomes blocked.

Hereinafter, the coupling half 200 can also be referred to as a body 200 or as a first coupling 200, and the coupling half 300 can also be referred to as an insert 300 or as a second coupling 300. The use of the nomenclature of body 200 and insert 300 will also be used to identify some of the components of the body 200 and the insert 300.

Figure 14:
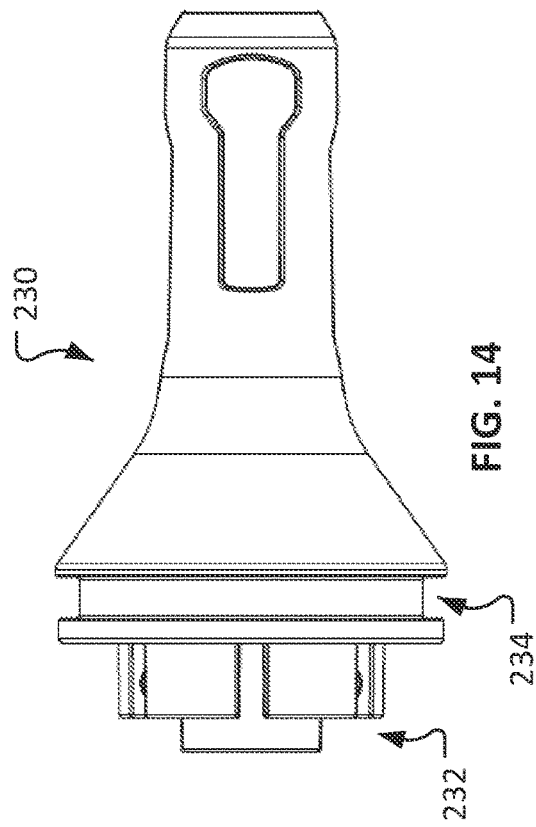
FIGS. 14-16 show various views of a body valve component of the fluid coupling system of FIG. 1.
Figure 15:
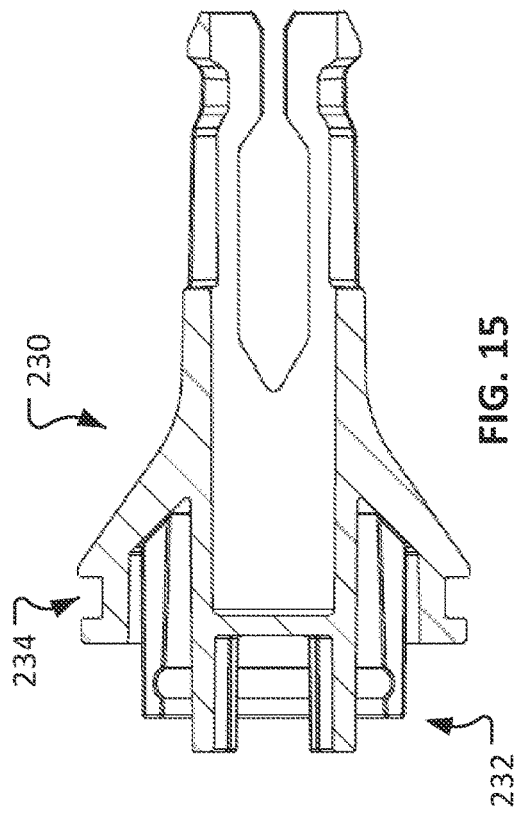
Figure 16:
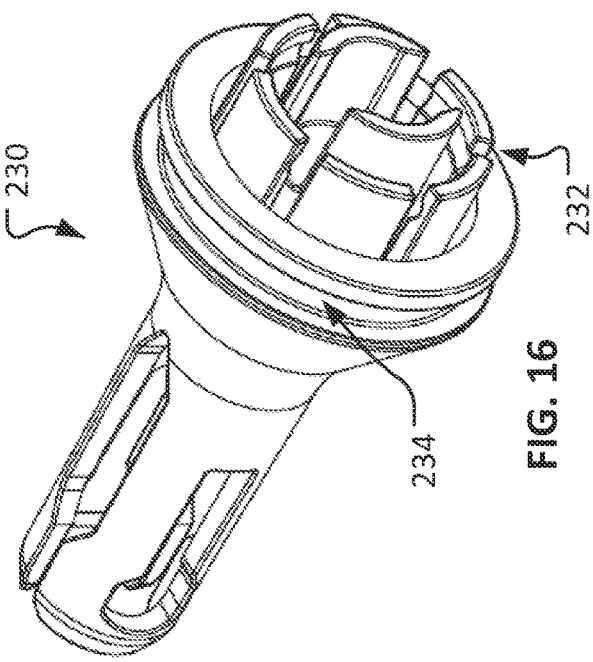
Figure 19:
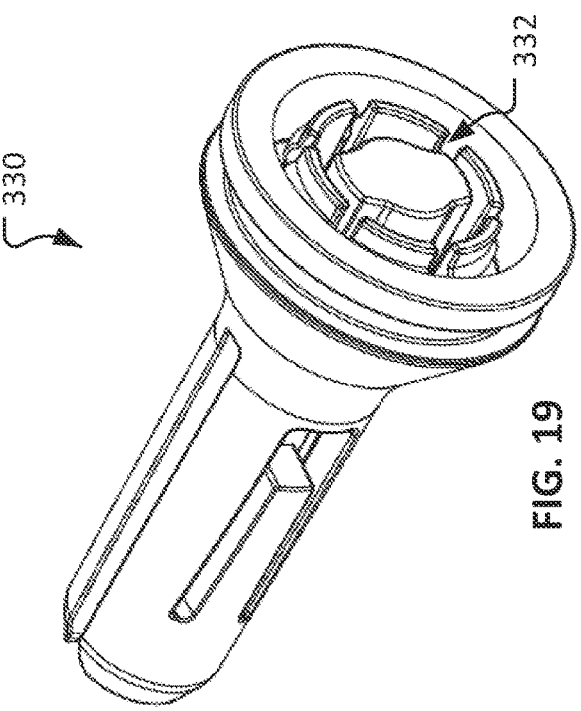
FIGS. 17-19 show various views of an insert valve component of the fluid coupling system of FIG. 1.
Figure 17:
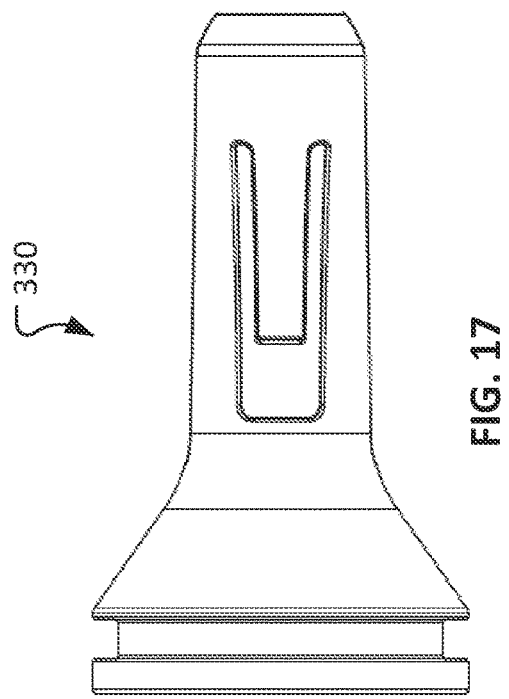
Figure 18:
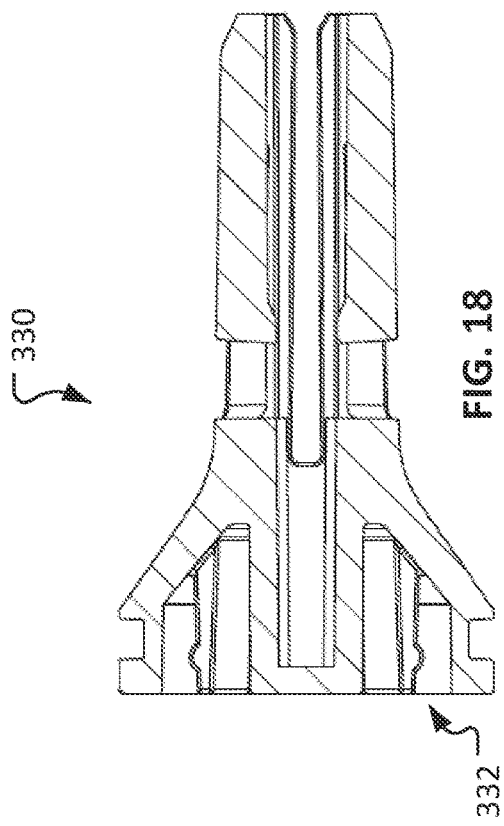
Figure 22:
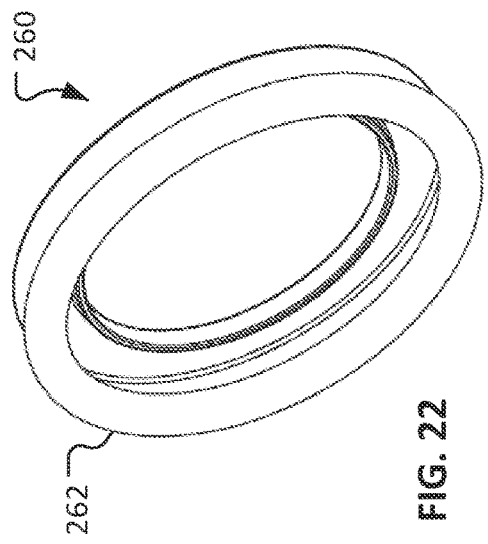
FIGS. 20-23 show various views of a body valve gasket of the fluid coupling system of FIG. 1.
Figure 23:
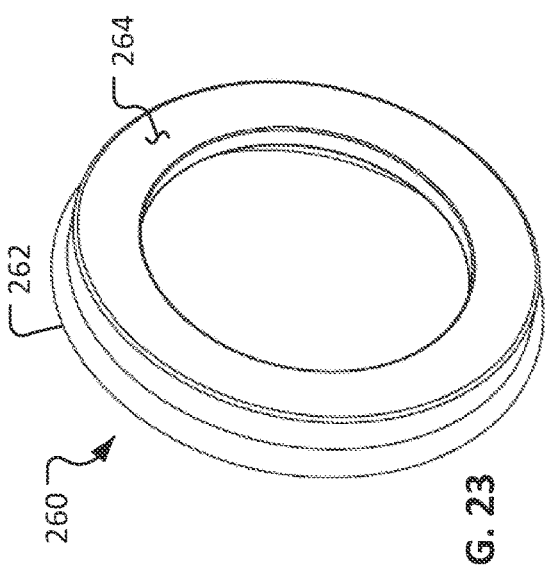
Figure 20:
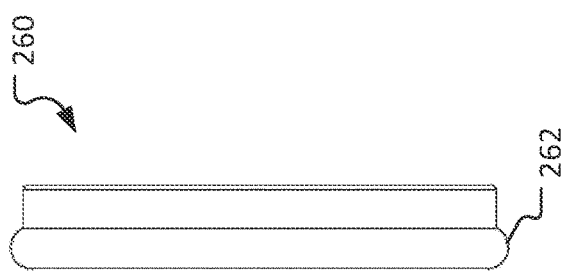
Figure 21:
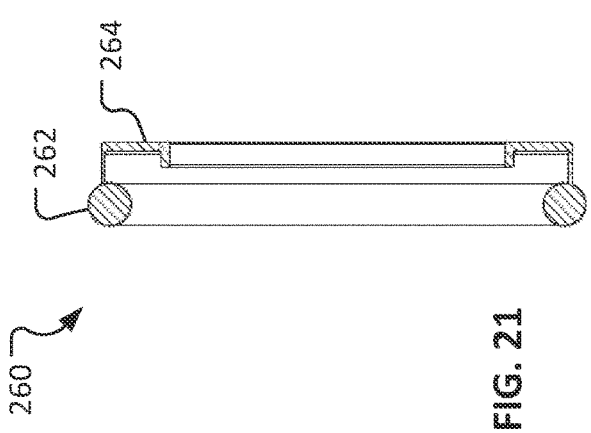

As shown, for example, in FIGS. 5 and 7, the body 200 includes a body valve 230, and the insert 300 includes an insert valve 330. The body valve 230 is shown in isolation in FIGS. 14-16, and the insert valve 330 is shown in isolation in FIGS. 17-19. The front face 232 of the body valve 230 and the front face 332 of the insert valve 330 have complimentary structures by which the body valve 230 and the insert valve 330 are releasably coupled to each other (e.g., as shown in FIGS. 3,5, and 7) until the body 200 is separated from the insert 300. In addition, a body valve gasket 260 (FIGS. 20-23) that is coupled with the body valve 230 provides a face seal between the outer annular sealing surfaces of the front faces 232 and 332 of the body valve 230 and the insert valve 330.

The body valve gasket 260 has an annular portion 262 that is seated in a seal groove 234 defined by the body valve 230. The body valve gasket 260 also has a face seal portion 264 that provides a seal between the front face 232 of the body valve 230 and the front face 332 of the insert valve 330. The seal provided by the face seal portion 264 positioned between the front face 232 of the body valve 230 and the front face 332 of the insert valve 330 advantageously contributes to the non-spill performance feature of the fluid coupling assembly 100 by preventing fluid ingress between the body valve 230 and the insert valve 330.

While the fluid coupling assembly 100 is in the operable configuration as shown in FIGS. 1-3, for example, the body valve 230 and the insert valve 330 are both in their open configuration (so that the open fluid flow path 103 exists). However, after a sufficient amount of rotation of the shell 250 (e.g., as indicated by the arrow 106 in FIG. 6), the body valve 230 and the insert valve 330 both transition to their closed configuration (so that the open fluid flow path 103 no longer exists). This closed configuration is visible in FIG. 7, for example. The closed configuration results because the rotation of the shell 250 drives a longitudinal translation of the insert 300 (other than the insert valve 330) and a shuttle 240 farther into the body 200.

Figure 24:
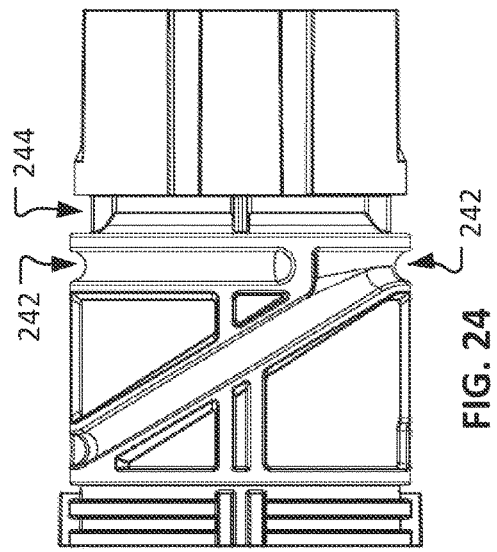
FIGS. 24-26 show various views of a shuttle component of the fluid coupling system of FIG. 1.
Figure 25:
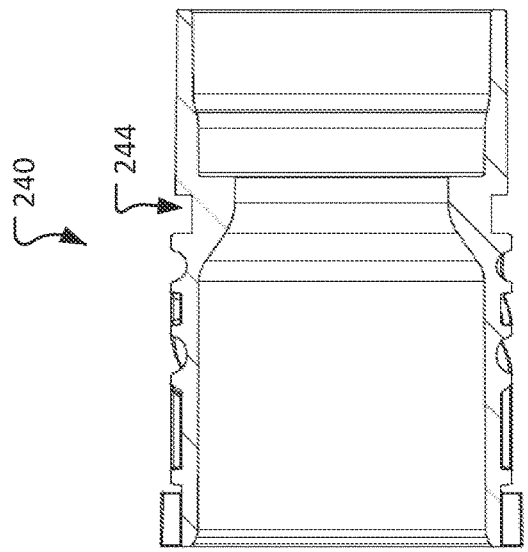
Figure 26:
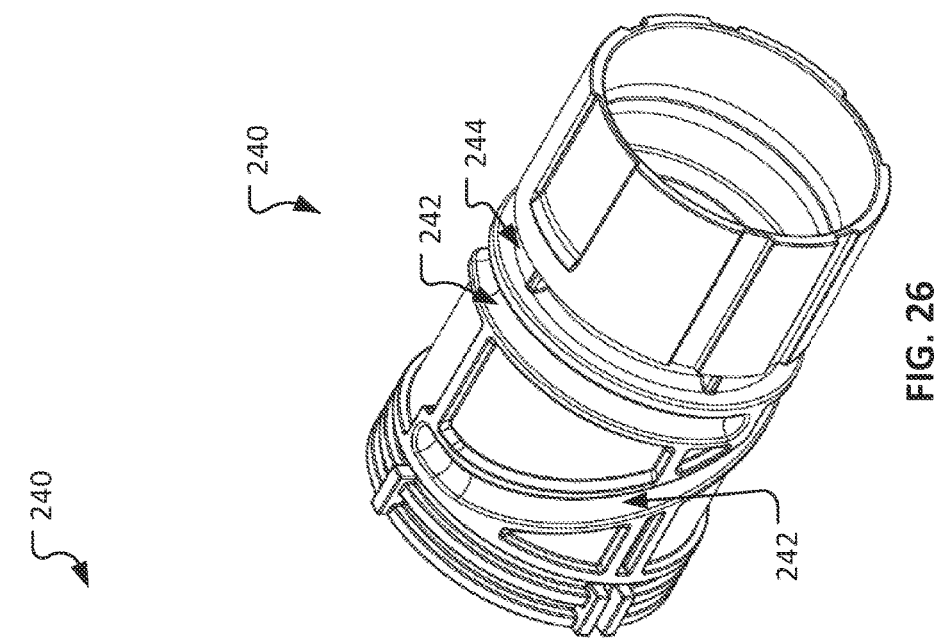

The shuttle 240 is shown in isolation in FIGS. 24-26. The shuttle 240 is an open cylinder. As visible in FIGS. 5 and 7, the body valve 230 and the insert valve 330 are located within the open interior space defined by the shuttle 240 while the fluid coupling assembly 100 is in the operable configuration.

The shuttle 240 also defines grooves 242 that include a spirally-extending portion and a circumferentially—extending portion. The grooves 242 slidably receive corresponding projections 254 (FIG. 12) that extend radially inward from the cylindrical housing of the shell 250. Accordingly, rotations of the shell 250 cause the projections 254 to move within the grooves 242 of the shuttle 240 (because the shuttle 240 is restrained from rotating while being free to translate longitudinally). While the projections 254 are moving within the spirally-extending portions of the grooves 240 as a result of the rotation of the shell 250, the shuttle 240 is therefore forced to longitudinally translate. Sufficient continuation of this longitudinal translation of the shuttle 240 reconfigures the fluid coupling assembly 100 from the operable/open configuration shown in FIGS. 1-3 to the closed configuration shown in FIGS. 6 and 7.

Figure 27:
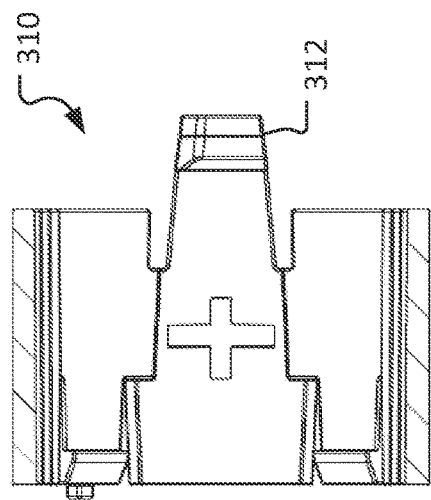
FIGS. 27-29 show various views of an insert housing component of the fluid coupling system of FIG. 1.
Figure 28:
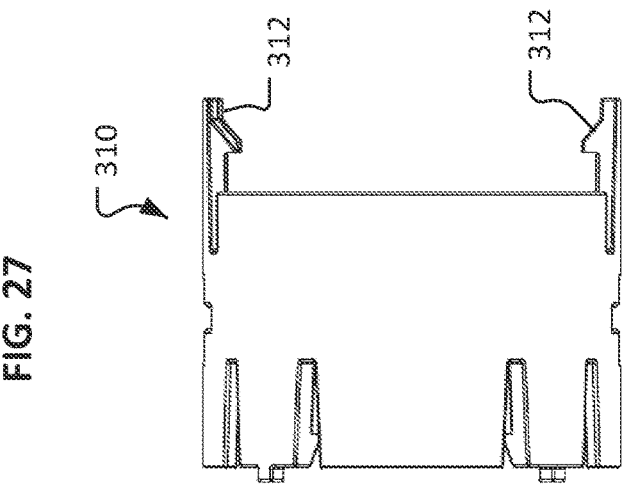
Figure 29:
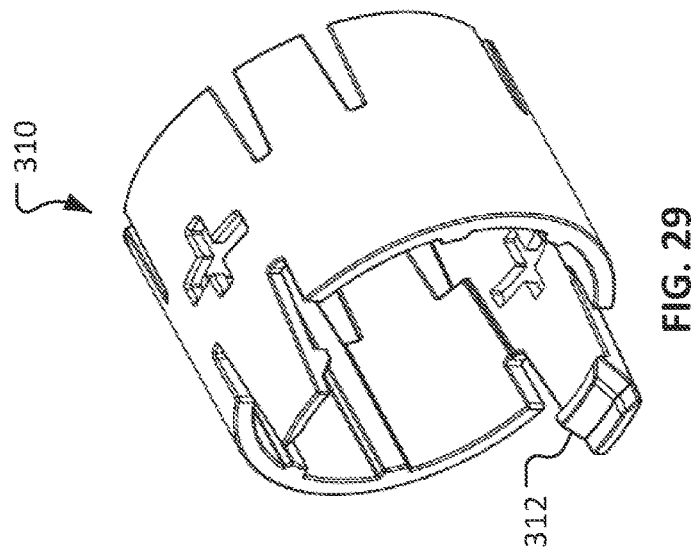
Figure 32:
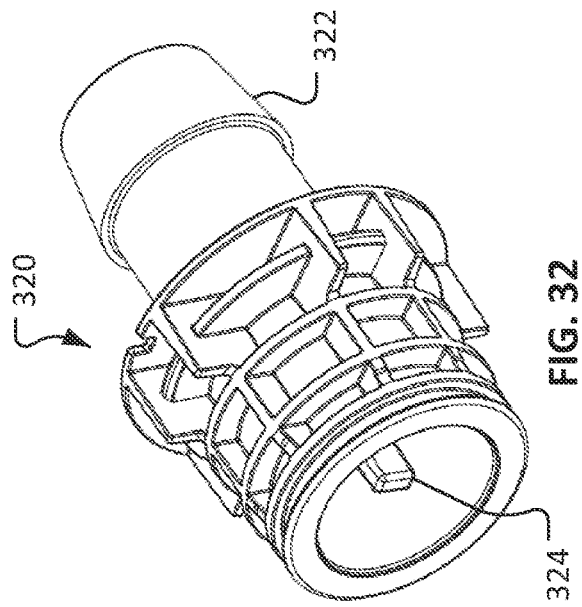
FIGS. 30-32 show various views of an insert termination component of the fluid coupling system of FIG. 1.
Figure 30:
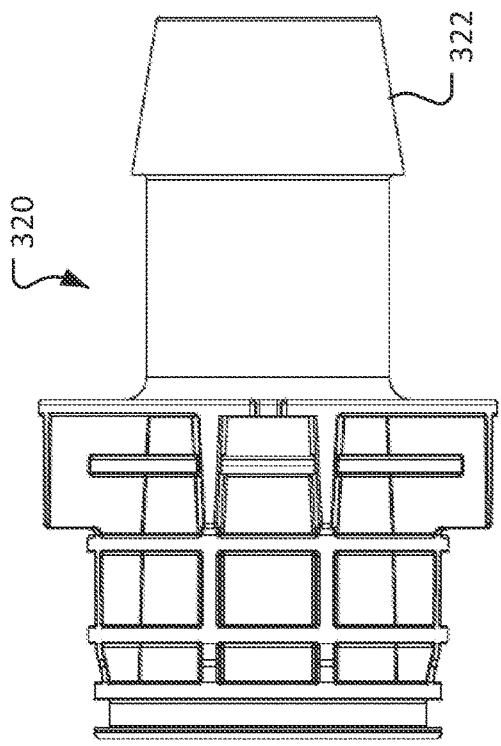
Figure 31:
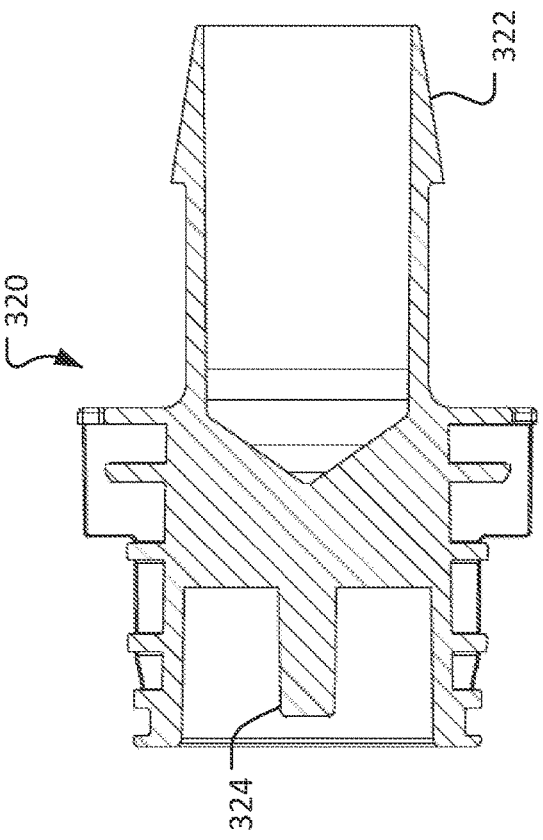

As the shuttle 240 is being longitudinally translated as a result of the manual rotation of the shell 250, the shuttle 240 longitudinally pulls along with it an insert housing 310 (shown in isolation in FIGS. 27-29) and an insert termination 320 (shown in isolation in FIGS. 30-32) that are releasably coupled to the shuttle 240. The insert termination 320 includes a center post 324 that is slidably coupled with the insert valve 330. Accordingly, as the insert termination 320 is being translated as a result of the rotation of the shell 250 and translation of the shuttle 240, the insert termination 320 slides in relation to the insert valve 330. This is evident by comparing FIG. 5 with FIG. 7.

The second step in the sequence of steps to disconnect the coupling halves 200 and 300 is completed with the closure/sealing of the body valve 230 relative to the shuttle 240 and the insert valve 330 relative to the insert termination 320.

Figure 8:
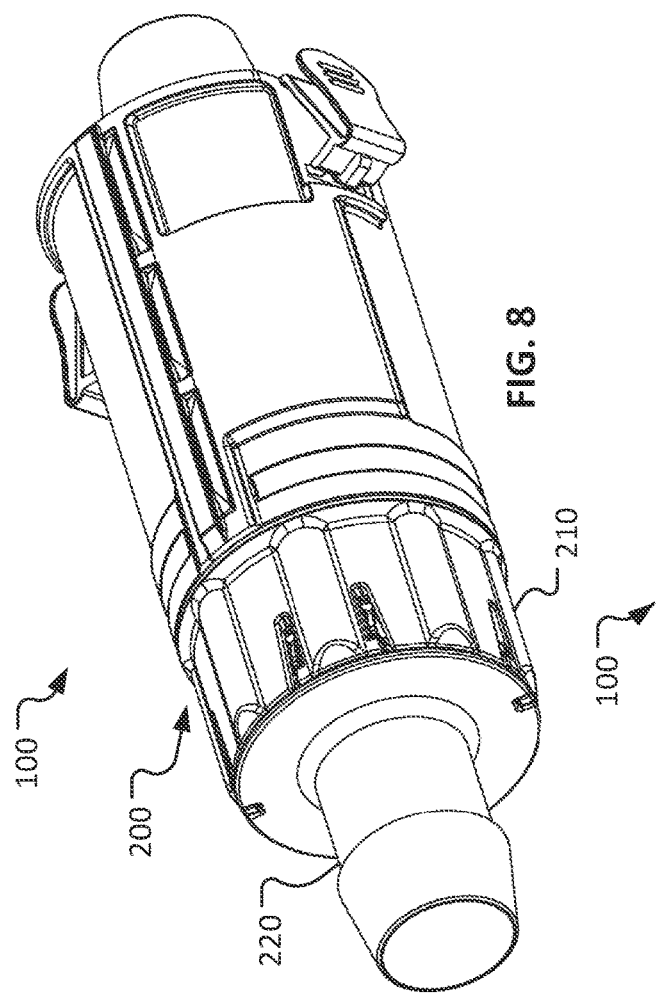
FIG. 8 is a perspective view of the fluid coupling system of FIG. 1 configured in a third stage of disconnection.
Figure 9:
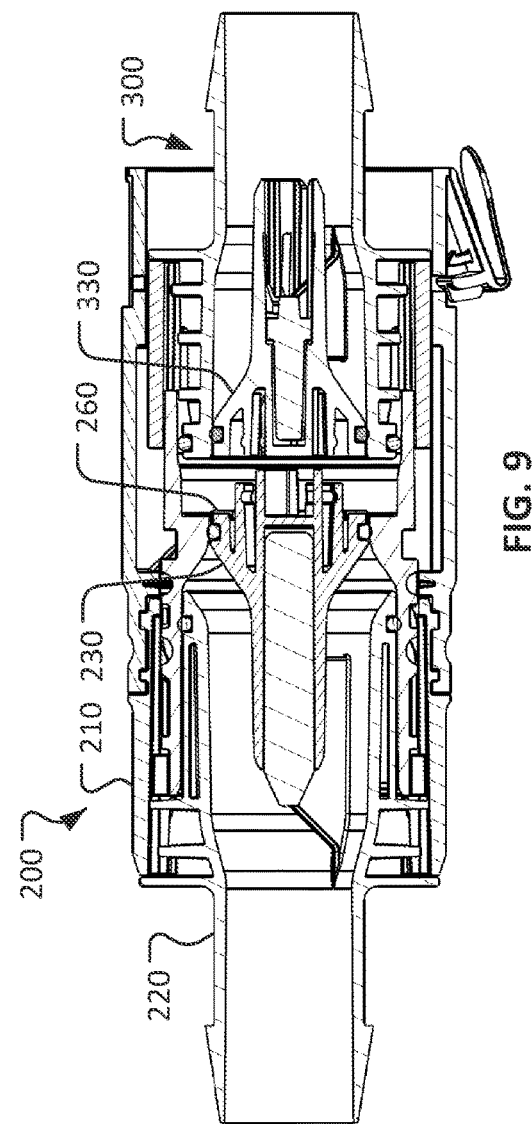
FIG. 9 is a longitudinal cross-section view of the fluid coupling system configured as in FIG. 8.

After the fluid coupling assembly 100 reaches the closed configuration shown in FIGS. 6 and 7, then continued/additional rotation of the shell 250 reconfigures the fluid coupling assembly 100 to the arrangement shown in FIGS. 8 and 9. In the configuration shown in FIGS. 8 and 9 the front faces 232 and 332 of the body valve 230 and the insert valve 330 have become unengaged and physically separated from each other.

The separation of the body valve 230 and the insert valve 330 (as visible in FIG. 9) occurs as follows. As shown in FIGS. 7 and 27-29, the insert housing 310 includes two flexible cantilevered arms 312 that are originally engaged with a recess 244 (FIGS. 24-26) defined by the shuttle 240. However, as the insert housing 310 is translated as a result of the rotation of the shell 250, the cantilevered arms 312 eventually come into contact with compound ramps 256 located on the inner diameter surface of the shell 250 (see FIG. 12). The compound ramps 256 exert radially outward forces on the cantilevered arms 312 to elastically deflect the cantilevered arms 312 radially outward into recess regions 258 defined by the inner diameter surface of the shell 250. The radially outward deflection of the cantilevered arms 312 uncouples the insert housing 310 from the shuttle 240. This is evident by comparing FIG. 7 with FIG. 9.

In another configuration, the cantilevered arms 312 may deflect as a result of contact with ramps on the body housing 210 instead of the body shell 250. In such a case, the longitudinal travel of the shuttle 240 causes the deflection, rather than rotational travel of shell 250.

During this third step in the sequence of steps to disconnect the coupling halves 200 and 300, as the compound ramps 256 exert force on cantilevered arms 312, a sliding O-ring seal between the insert termination 320 and the shuttle 240 is moved longitudinally from an area of high compression (sealed) to an area of low compression (released) within the shuttle 240.

Figure 10:
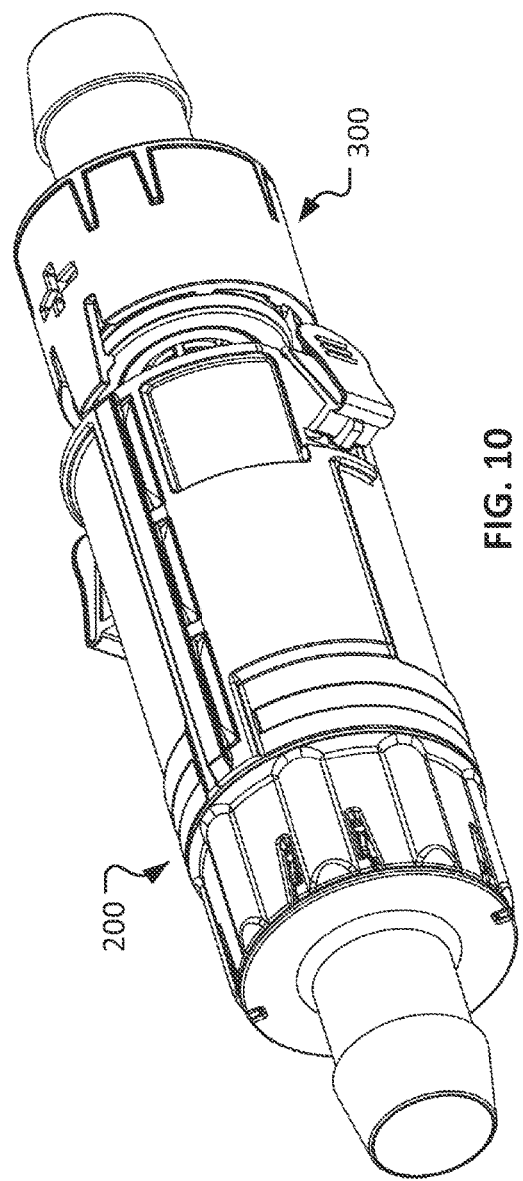
FIG. 10 is a perspective view of the fluid coupling system of FIG. 1 configured in a fourth and final stage of disconnection.
Figure 11:
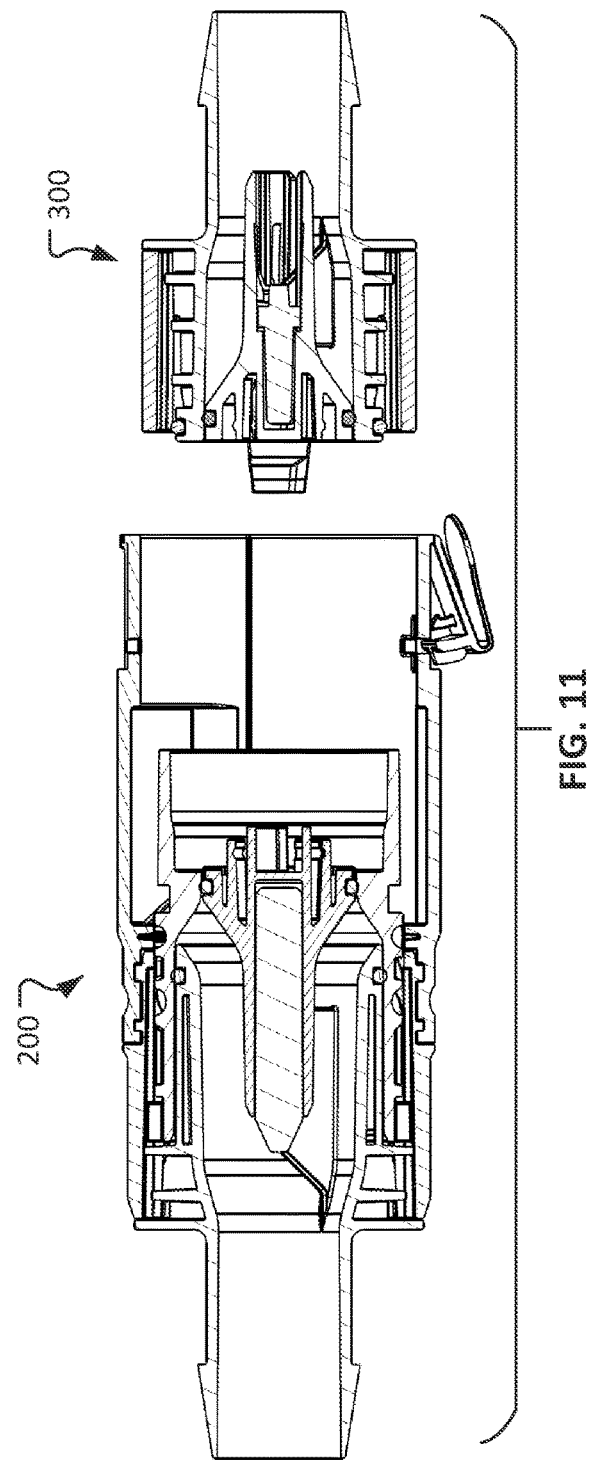
FIG. 11 is a longitudinal cross-section view of the fluid coupling system configured as in FIG. 10.

Further rotation of the shell 250 (while the cantilevered arms 312 of the insert housing 310 are disengaged from the shuttle 240) then results in the compound ramps 256 exerting longitudinal forces against the cantilevered arms 312 to force the insert housing 310 to move longitudinally away from the body 200. Referring to FIGS. 10 and 11, further rotation of the shell 250 (while the cantilevered arms 312 of the insert housing 310 are disengaged from the shuttle 240) then results in the compound ramps 256 exerting longitudinal forces against the cantilevered arms 312 to force the insert housing 310 to move longitudinally away from the body 200.

The third step in the sequence of steps to disconnect the coupling halves 200 and 300 is completed with the uncoupling of the insert housing 310 from the shuttle 240, and the longitudinal separation of the front faces 232 and 332 of the body valve 230 and the insert valve 330.

The fourth and final step in the sequence of steps to disconnect the coupling halves 200 and 300 is completed with the manual longitudinal separation of the body 200 from the insert 300 as shown in FIGS. 10 and 11. This is evident by comparing FIG. 9 with FIG. 11.

Figure 38:
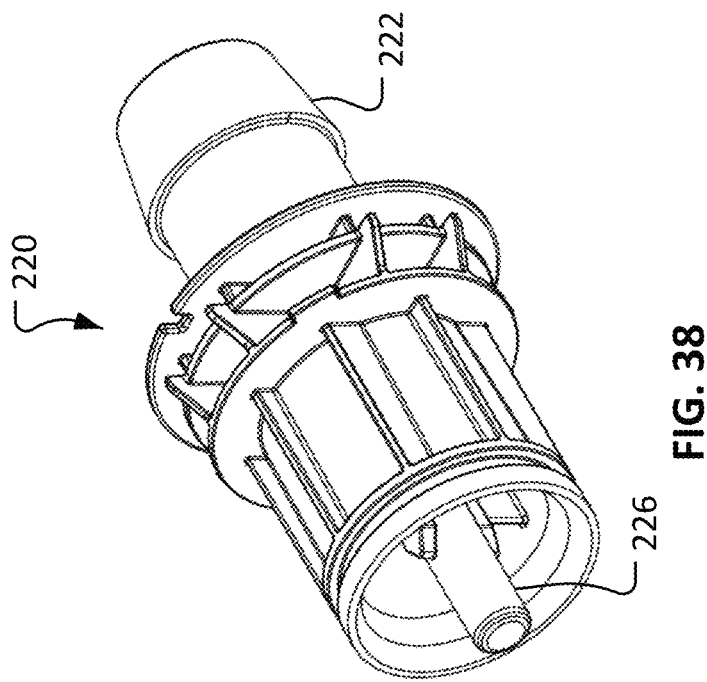
FIGS. 36-38 show various views of a body termination component of the fluid coupling system of FIG. 1.
Figure 36:
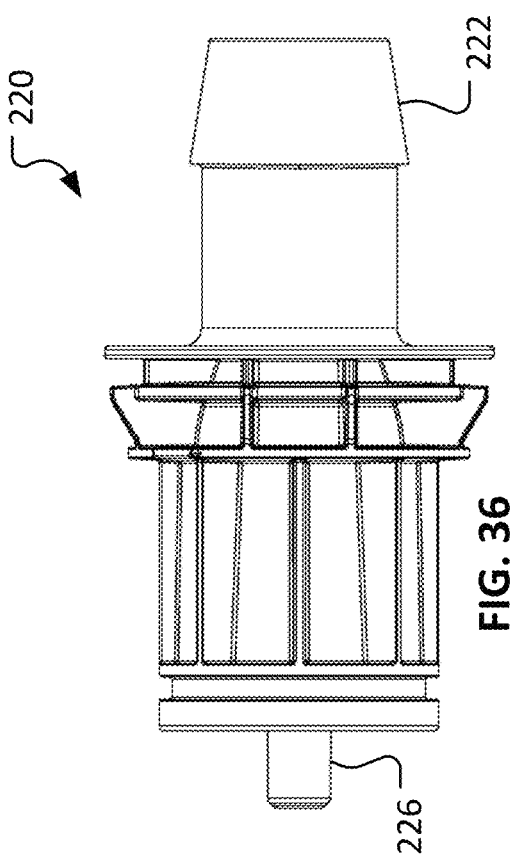
Figure 37:
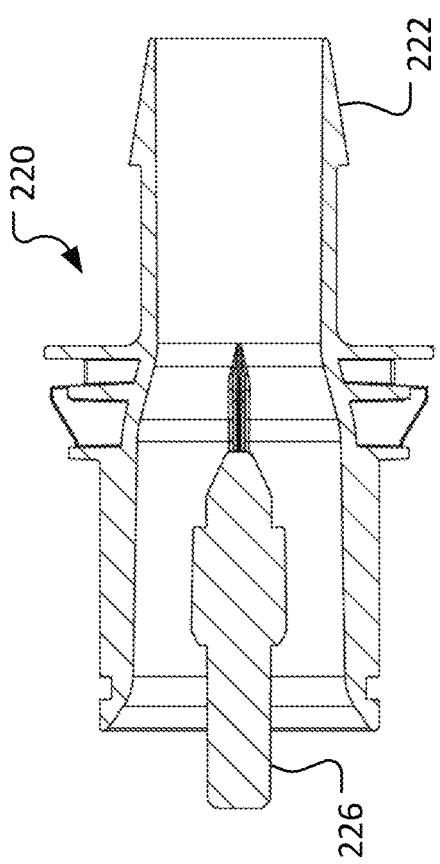

The body 200 also includes the body housing 210 (FIGS. 33-35) and the body termination 220 (FIGS. 36-38). The body valve 230 is fixedly coupled to a center post 226 of the body termination 220. A front face of the body housing 210 is configured with an annular saw tooth pattern 212. In another configuration, the ratchet and pawl mechanism may be reversed. That is, the saw tooth pattern 212 may be placed on the shell 250, with the flexible pawl extending from the body housing 210.

The saw tooth pattern 212 engages with a pawl 259 (FIG. 12) of the shell 250 to comprise a one-way rotation mechanism. That is, in a general sense, the shell 250 can only be rotated in one direction relative to the body 200 and insert 300 because of the ratchet and pawl mechanism provided by the saw tooth pattern 212 of the body housing 210 and the pawl 259 of the shell 250. However, more precisely, it should be understood that the ratchet and pawl mechanism provided by the saw tooth pattern 212 and the pawl 259 allows for a small amount of rotation of the shell 250 in the reverse direction. The amount of rotation in the reverse direction is limited by the size of the teeth of the saw tooth pattern 212. That is, the shell 250 can be rotated in the reverse direction by up to, but no more than, the width of a single tooth of the saw tooth pattern 212.

Moreover, the saw tooth pattern 212 is selectively designed and configured with a specific number of teeth and specific size of teeth so that each increment of rotation of the shell 250 (as determined by an individual tooth of the saw tooth pattern 212) corresponds to a desired distance of translation of the shuttle 240 and/or to a maximum allowable amount of reverse rotation of the shell 250. For example, in some embodiments the maximum allowable amount of reverse rotation of the shell 250 is determined by the width of the sealing surface of a seal 224 (FIG. 5) that is radially compressed in a location between the shuttle 240 and the body termination 220. By limiting the maximum allowable amount of reverse rotation of the shell 250, the reverse translation of the shuttle 240 in relation to the seal 224 of the body termination 220 can be limited to no more than the width of the sealing surface of the seal 224, thereby prevented contamination from entering the fluid-wetted interior regions of the fluid coupling assembly 100.

The body 200 includes the body housing 210, the body termination 220, the body valve 230, the shuttle 240, the shell 250, and the body valve gasket 260. The shell 250 is rotatably coupled to the body housing 210. The body housing 210 is fixedly coupled to the body termination 220. The body valve 230 is fixedly coupled to the body termination 220. The shuttle 240 is disposed about the body valve 230 and movable (longitudinally translatable) relative to the body valve 230 between an open configuration and a closed configuration. The closed configuration is attained by rotating the shell 250, which drives the shuttle 240 to longitudinally from the open configuration to the closed configuration. The shuttle 240 does not rotate as it is being translated.

The insert 300 includes the insert housing 310, the insert termination 320, and the insert valve 330. The insert housing 310 is fixedly coupled to the insert termination 320. The insert valve 330 is movably coupled to the insert termination 320 such that the insert valve 330 is longitudinally translatable relative to the insert termination 320 along the longitudinal axis between an open configuration and a closed configuration.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system modules and components in the embodiments described herein should not be understood as requiring such separation in all embodiments.

What is claimed is:

1. A single-use aseptic fluid coupling assembly defining a longitudinal axis and an open fluid flow path through the fluid coupling assembly along the longitudinal axis, the fluid coupling assembly comprising:
   a first coupling comprising:
      a first housing;

a first termination member fixedly coupled to the first housing and including a first termination;
a shell that is rotatably coupled to the first housing;
a first valve that is fixedly coupled to the first termination member; and
a shuttle disposed about the first valve, the shuttle being coupled to the shell such that the shuttle is translatable along the longitudinal axis in response to rotation of the shell; and
a second coupling releasably connected to the first coupling and comprising:
a second housing;
a second termination member fixedly coupled to the second housing and including a second termination; and
a second valve movably coupled to the second termination, the second valve being translatable along the longitudinal axis relative to the second termination,
wherein the first valve is releasably latched to the second valve.

2. The fluid coupling assembly of claim 1, wherein the fluid coupling assembly is metallic-free.

3. The fluid coupling assembly of claim 1, further comprising a valve gasket compressed between an outer annular face portion of the first valve and an outer annular face portion of the second valve.

4. The fluid coupling assembly of claim 1, wherein the shell includes one or more projections that are movably disposed in one or more slots defined by the shuttle.

5. The fluid coupling assembly of claim 4, wherein the one or more slots each include: (i) a spirally-extending portion and (ii) a circumferentially-extending portion.

6. The fluid coupling assembly of claim 1, wherein the shuttle is releasably coupled to the second housing.

7. The fluid coupling assembly of claim 1, wherein the first coupling is separable from the second coupling by rotating the shell and then longitudinally separating the first and second couplings from each other.

8. The fluid coupling assembly of claim 7, wherein the rotating the shell unlatches the first valve from the second valve.

9. The fluid coupling assembly of claim 7, wherein the rotating the shell uncouples the shuttle from the second housing.

10. The fluid coupling assembly of claim 7, wherein the first and second couplings cannot be separated from each other until: (i) the first valve is in a closed configuration relative to the shuttle and (ii) the second valve is in a closed configuration relative to the second termination member.

11. The fluid coupling assembly of claim 10, wherein the rotating the shell moves the first and second valves to the closed configurations.

12. A single-use aseptic fluid coupling assembly defining a longitudinal axis and an open fluid flow path through the fluid coupling assembly along the longitudinal axis, the fluid coupling assembly comprising:
a first coupling comprising:
a first housing;
a shell that is rotatably coupled to the first housing; and
a first valve; and
a second coupling releasably connected to the first coupling and comprising:
a second housing; and
a second valve, the second valve being translatable along the longitudinal axis,
wherein the first valve is releasably latched to the second valve, and
wherein, once the first and second couplings have been unconnected from each other, the first and second couplings cannot be reconnected to define the open fluid flow path.

13. The fluid coupling assembly of claim 12, wherein the shell includes one or more projections that are movably disposed in one or more slots defined by a shuttle.

14. The fluid coupling assembly of claim 13, wherein the first coupling further comprises the shuttle disposed about the first valve, the shuttle being coupled to the shell such that the shuttle is translatable along the longitudinal axis in response to rotation of the shell.

15. The fluid coupling assembly of claim 12, further comprising a valve gasket compressed between an outer annular face portion of the first valve and an outer annular face portion of the second valve.

16. The fluid coupling assembly of claim 12, wherein the fluid coupling assembly is metallic-free.

17. The fluid coupling assembly of claim 12, wherein the first and second couplings cannot be unconnected from each other until both the first valve and the second valve are in a closed configuration.

* * * * *